United States Patent [19]
Patapanian et al.

[11] Patent Number: 5,624,478
[45] Date of Patent: Apr. 29, 1997

[54] ETHYLENE ABSORPTION DEVICE

[76] Inventors: Edward Patapanian, 52 Stony Brook Rd., Belmont, Mass. 02178; Cheryl Rieves, 25664 Donald Ave., Hayward, Calif. 94544

[21] Appl. No.: 528,373

[22] Filed: Sep. 14, 1995

[51] Int. Cl.$^6$ .................................................. B01D 53/04
[52] U.S. Cl. .......................... 96/108; 96/148; 96/154; 422/122; 426/419
[58] Field of Search .................... 95/144; 96/108, 96/135, 138, 147, 148, 153, 154; 206/0.6; 426/418, 419; 239/54–57; 422/5, 28, 122

[56] References Cited

U.S. PATENT DOCUMENTS

| | | | |
|---|---|---|---|
| 2,001,828 | 5/1935 | Smith | 96/147 |
| 2,765,046 | 10/1956 | Rondholz | 96/148 X |
| 3,246,758 | 4/1966 | Wagner | 96/108 X |
| 3,706,410 | 12/1972 | Baker | 426/419 X |
| 4,055,672 | 10/1977 | Hirsch et al. | 426/418 X |
| 4,235,750 | 11/1980 | Cazalet | 426/419 X |
| 4,256,773 | 3/1981 | Itoga et al. | 95/144 X |
| 4,333,752 | 6/1982 | Thies et al. | 96/138 X |
| 4,612,026 | 9/1986 | Pollara et al. | 96/135 |
| 4,614,528 | 9/1986 | Lennen | 96/147 |
| 4,906,398 | 3/1990 | Alvarez et al. | 426/419 X |
| 5,009,308 | 4/1991 | Cullen et al. | 96/154 X |
| 5,234,162 | 8/1993 | Sullivan | 239/55 X |
| 5,443,626 | 8/1995 | Kiyani | 96/108 |
| 5,451,248 | 9/1995 | Sadkowski et al. | 95/144 X |
| 5,468,447 | 11/1995 | Bermas | 422/122 X |
| 5,500,038 | 3/1996 | Dauber et al. | 96/153 X |

FOREIGN PATENT DOCUMENTS

| | | | |
|---|---|---|---|
| 3613884 | 10/1987 | Germany | 96/108 |
| 4025589 | 2/1992 | Germany | 96/108 |
| 49-066433 | 6/1974 | Japan | 426/419 |
| 63-162023 | 7/1988 | Japan | 96/154 |
| 63-283719 | 11/1988 | Japan | 96/135 |
| 1-015112 | 1/1989 | Japan | 96/135 |
| 1-315310 | 12/1989 | Japan | 96/154 |
| 2-229522 | 9/1990 | Japan | 96/154 |
| 3-221114 | 9/1991 | Japan | 96/154 |
| 3-229610 | 10/1991 | Japan | 96/154 |
| 5-076720 | 3/1993 | Japan | 96/108 |
| 6-319935 | 11/1994 | Japan | 96/154 |
| 1550960 | 8/1979 | United Kingdom | 96/135 |
| 2210806 | 6/1989 | United Kingdom | 96/154 |

OTHER PUBLICATIONS

"Ethysorb's formula for profit", Stay Fresh Ltd., 11 page brochure, Aug. 3, 1981.

*Primary Examiner*—Robert Spitzer
*Attorney, Agent, or Firm*—Scott B. Garrison; Gary E. Lambert

[57] ABSTRACT

The purpose of this invention is to provide a consumer with an inexpensive and reliable device for controlling ethylene gas for plantstuffs. The device is a sealed, air tight package which contains a gas permeable envelope containing ethylene absorbing chemicals. A consumer peels a seal off of the airtight packaging thereby allowing the chemical reagents to be exposed to the atmosphere within the container in which the ethylene producer is situated. Only upon initial activation by the consumer does the reaction take place. The system is simple, reliable, inexpensive and disposable.

8 Claims, 1 Drawing Sheet

ETHYLENE ABSORPTION DEVICE

BACKGROUND OF THE INVENTION

The present invention relates to the field of preservation of plantstuffs. More particularly, it relates to the preservation of produce, flowers and other plants by the control and absorption of ethylene gas.

One problem with storage of produce and flowers is that ethylene gas is released from the plant into the surrounding atmosphere. Ethylene gas is a natural ripening agent of many of these plants. In order to slow the ripening process, some means of controlling ethylene production is needed. It is well known in the industry that certain chemicals absorb or otherwise eliminate ethylene gas. Combinations of potassium permanganate and alumina, or a hydrated combination of potassium permanganate and zeolite are two such products. Each readily absorbs ethylene gas resulting in a substantial delay in the ripening process. An additional benefit of these chemicals is that they also absorb odors.

The typical industrial consumer of ethylene reducing systems purchases large quantities of an ethylene absorbent product. An industrial system usually circulates the air within the storage facility through filters having the product imbedded in the filter. However, this method would not be cost effective nor feasible for home use. Although it has recently been made possible for individuals to purchase products containing small quantities of potassium permanganate and zeolite for home use, these products usually have shortened shelf lives due to the chemicals being adversely affected by the packaging.

One manufacturer of such a product packages the chemical combination in a heavy paper container. However, such a container has a disadvantage in that the container cannot preserve the potency of the chemical during storage because a paper or cardboard container is permeable to air. Until the present invention, there has not been an inexpensive, reliable nor suitable product available to the individual to reduce ethylene gas.

SUMMARY OF THE INVENTION

The present invention relates to a device for the preservation of produce, flowers and other plants by directly absorbing the ethylene gas produced by said plantstuffs. Additionally, the device absorbs odors generated by plantstuffs as well. The device comprises a gas permeable container containing a quantity of an ethylene absorbent such as a hydrated combination of potassium permanganate and zeolite. The gas permeable container is packaged in an airtight containment device. Only upon activation of the device which occurs when the consumer breaks the seal on the containment device do the chemicals begin to absorb ethylene.

It is therefore an object of the present invention to provide an improved device for absorbing ethylene gas which stores the absorbing chemical and preserves its potency until activation by the consumer.

It is another object of this invention to provide a containment device for ethylene absorbents which can be used by the consumer in a non-industrial application to reduce ethylene gas levels in refrigerators or the like.

It is another object of this invention to provide an improved device for absorbing ethylene gas that is both inexpensive to manufacture and simple to use.

It is yet another object of this invention to provide a disposable system which can be replaced by the consumer after a predetermined amount of time has elapsed.

It is yet another object of this invention to provide a system which absorbs and eliminates unwanted odors.

BRIEF DESCRIPTION OF THE DRAWINGS

The novel features considered characteristic of the invention are set forth in the appended claims. The invention itself, however, both as to its construction and its method of operation, together with additional objects and advantages thereof, will best be understood from the following description of the specific embodiments when read and understood in connection with the accompanying drawing.

DESCRIPTION OF THE PREFERRED EMBODIMENT

Figure 1:
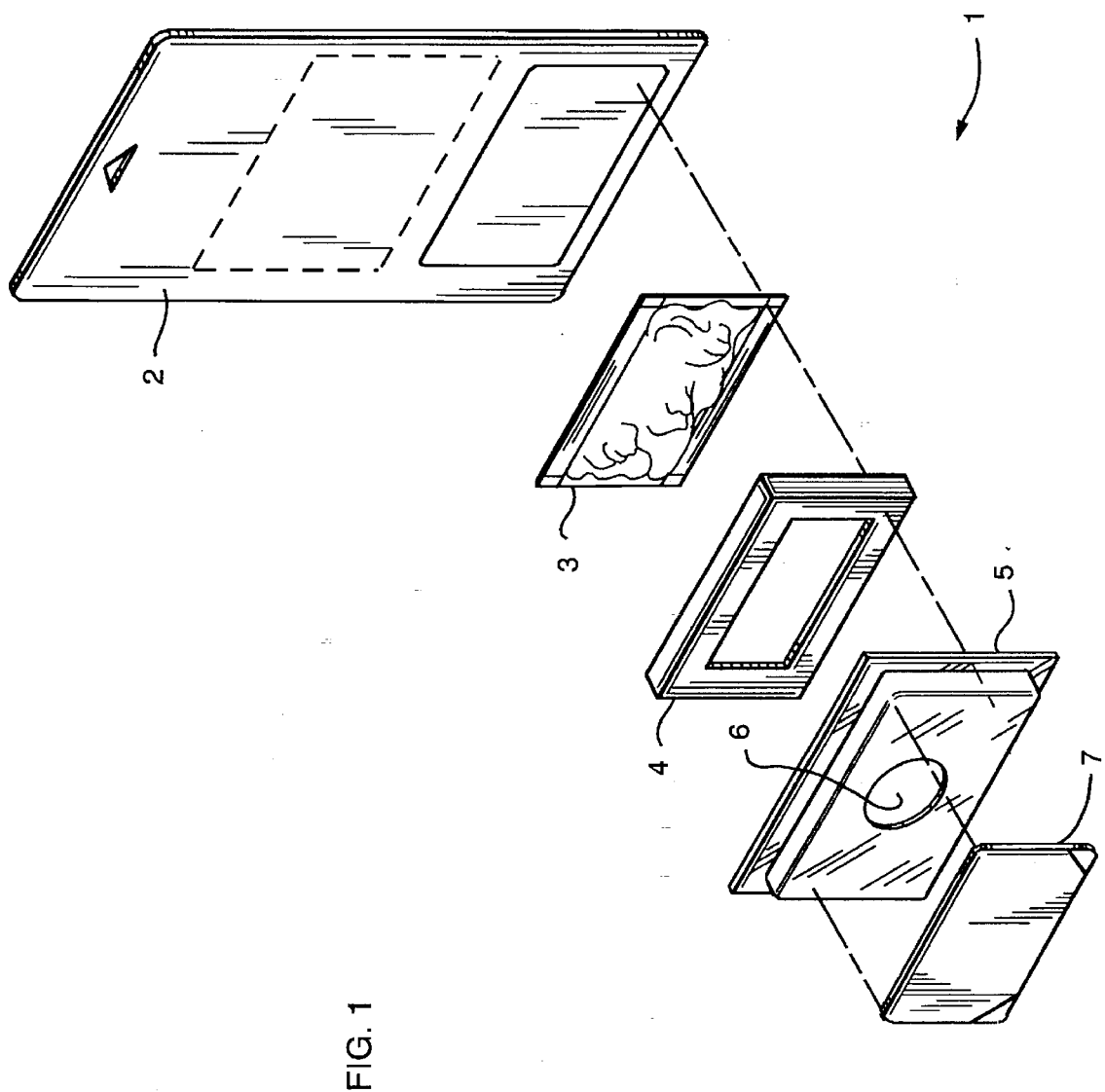
FIG. 1 is an exploded view of the ethylene absorption device constructed in accordance with the present invention.

With reference to FIG. 1, a device for the storage and use of ethylene absorbing chemicals by the non-industrial consumer is indicated generally at 1.

The preferred embodiment of the device is constructed to store and maintain the potency of a combination of chemicals, in particular, combinations of potassium permanganate and alumina, or hydrated combinations of potassium permanganate and zeolite. It is contemplated that this device comprise an essentially flat air tight container having a backing 2, a gas permeable envelope 3 containing said chemicals, a containment structure 4 which can be made of heavy paper in which envelope 3 is set, a semi-rigid access panel 5 containing window 6 through which the absorption process is directed, and an air tight seal 7 which can be made of a metallized polyester, a metal foil or the like to seal access window 6 until the consumer activates the device.

It is contemplated that a consumer having obtained the device will peel seal 7 back from access panel 5 thereby exposing envelope 3 containing the requisite chemicals to the atmosphere. Air reaches envelope 3 through access window 6. Containment structure 4 is contemplated to provide additional rigidity to access panel 5 without obliging the manufacturer of the device to create a stronger access panel. Containment structure 4 and access panel 5 working in conjunction should provide adequate rigidity to the device to ensure that the device does not collapse under the normal loads to which the device is intended to be subjected. These loads to which the device should be subjected comprise inadvertent crushing by the consumer in opening the package and placing the package in its desired location, and impact of plantstuffs resting on or against the device.

Containment structure 4 is sized to provide adequate space for envelope 3 to loosely rest. To ensure maximum efficiency of the device, envelope 3 should be loosely stored in containment structure 4 in such a manner as to permit air contact around envelope 3, not just the portion of envelope 3 that is directly in contact with access window 6.

It is contemplated that access panel 5 be a thin yet rigid plastic cover having a flanged base. The flanged base is suitable for seating as well as sealing said access panel to backing 2 thereby creating an airtight seal between backing 2 and access panel 5. Seal 7 prevents air from reaching envelope 3 until the user peels seal 7 from access panel 5 thus exposing envelope 3 to the air via access window 6. Seal 7 adheres to access panel 5 due to its surface being coated or otherwise impregnated with an adhesive, preferably a removable acrylic adhesive. Backing 2 can be sealed by a thin plastic coating applied to the backing material or by use of a foil backing to seal access panel 5 on the underside of access panel 5.

While the invention has been described and illustrated with reference to a specific embodiment thereof, it is understood that other embodiments may be resorted to without departing from the invention. Therefore the form of the invention set out above should be considered illustrative and not as limiting the scope of the following claims.

What is claimed is:

1. An ethylene absorption device comprising a backing, a gas permeable envelope containing ethylene absorbing chemicals, a containment means comprising a containment structure covered by an access panel wherein said access panel includes at least one opening therethrough which overlaps a similar opening through said containment structure, wherein said opening through each of said access panel and said containment structure enable free passage of air flow, wherein said access panel is otherwise generally impervious to air flow and said containment means traps and retain said envelope therein, and a sealing means for placement over said access panel to seal said containment means from atmosphere until said sealing means is removed.

2. A device according to claim 1 wherein said sealing means further comprises an adhesive backed foil.

3. A device according to claim 1 wherein said sealing means further comprises a metallized polyester.

4. A system for the absorption of ethylene gas in an atmospherically closed environment comprising:

a gas permeable envelope;

chemical reagents disposed in the envelope capable of absorbing ethylene gas;

a containment means for receiving and containing said envelope, the containment means loosely capturing said envelope, and further comprising a containment structure and an access panel, the containment structure is disposed within the access panel; wherein at least one opening is disposed through both the containment structure and the access panel enabling penetration of air through said opening onto said envelope;

a sealing means for sealing containment means, the sealing means preventing air from impinging upon the envelope until said sealing means is removed by user; and a backing to which the containment means is mounted.

5. A system as claimed in claim 4 wherein the access panel is a rigid air impervious material.

6. A system as claimed in claim 5 wherein the access panel is plastic.

7. A system as claimed in claim 4 wherein the sealing means is adhesive backed foil.

8. A system as claimed in claim 4 wherein the sealing means is a metallized polyester.

* * * * *